US010514328B2

United States Patent
Vandervalk et al.

(10) Patent No.: US 10,514,328 B2
(45) Date of Patent: Dec. 24, 2019

(54) METHOD AND SYSTEM FOR TESTING SURFACES FOR CONTAMINANTS

(71) Applicant: DeFelsko Corporation, Ogdensburg, NY (US)

(72) Inventors: Leon Vandervalk, Brockville (CA); Steven Nowell, Ogdensburg, NY (US); Nicholas Williams, Ogdensburg, NY (US)

(73) Assignee: DEFELKSO CORPORATION, Ogdensburg, NY (US)

( * ) Notice: Subject to any disclaimer, the term of this patent is extended or adjusted under 35 U.S.C. 154(b) by 90 days.

(21) Appl. No.: 15/415,625

(22) Filed: Jan. 25, 2017

(65) Prior Publication Data
US 2017/0261410 A1   Sep. 14, 2017

Related U.S. Application Data

(60) Provisional application No. 62/306,369, filed on Mar. 10, 2016.

(51) Int. Cl.
*G01N 1/28* (2006.01)
*G01N 1/38* (2006.01)
(Continued)

(52) U.S. Cl.
CPC ......... *G01N 1/28* (2013.01); *G01N 2001/028* (2013.01); *G01N 2001/1006* (2013.01); *G01N 2001/383* (2013.01)

(58) Field of Classification Search
CPC .... G01N 1/10; G01N 1/12; G01N 2001/1006; G01N 2001/028; G01N 2001/383; B01B 15/007
See application file for complete search history.

(56) References Cited

U.S. PATENT DOCUMENTS 2,660,053 A * 11/1953 Buehner ............... G01M 3/088
                                                                73/40
5,135,500 A *  8/1992 Zdeb ................. A61M 5/14526
                                                               604/131
(Continued)

FOREIGN PATENT DOCUMENTS

JP        2002333415 A   * 11/2002
JP   WO 2011115284 A1  *  9/2011   ............. G01N 27/06
(Continued)

OTHER PUBLICATIONS

Extended European Search Report issued in corresponding European Patent Application No. 17763688.3, dated Oct. 21, 2019 (8 pages).

(Continued)

*Primary Examiner* — Justin N Olamit
(74) *Attorney, Agent, or Firm* — Buchanan Ingersoll & Rooney PC

(57) ABSTRACT

The testing apparatus facilitates the testing of surfaces for contaminants such as soluble salts prior to applying a protective coating. The testing apparatus includes an air-permeable water-resistant membrane, an overlay, and a test chamber. When assembled, the testing apparatus provides an easily removable testing apparatus that encloses a void into which a solvent may be injected to determine the level of contamination of the surface.

19 Claims, 7 Drawing Sheets

(51) Int. Cl.
    *G01N 1/02*           (2006.01)
    *G01N 1/10*           (2006.01)

(56) References Cited

U.S. PATENT DOCUMENTS

| | | | |
|---|---|---|---|
| 5,346,557 A * | 9/1994 | Ito | H01L 21/02046 |
| | | | 134/10 |
| 5,610,514 A | 3/1997 | Ramaker | |
| 6,605,159 B2 * | 8/2003 | Joslyn | G01N 1/32 |
| | | | 134/18 |
| 8,252,600 B2 | 8/2012 | Jansen | |
| 9,128,002 B2 * | 9/2015 | Marino | G01M 3/02 |

FOREIGN PATENT DOCUMENTS

| | | |
|---|---|---|
| KR | 20120127727 A | 11/2012 |
| WO | 99/47916 A1 | 9/1999 |

OTHER PUBLICATIONS

Preparation of steel substrates before application of paints and related products—Tests for the assessment of surface cleanliness, Part 6: Extraction of soluble contaminants for analysis—The Bresle Method; International Standard—ISO 8502-6:2006, XO008087876 (14 pages) [Note: the Bresle method is discussed in detail in the specification of the present application].

* cited by examiner

METHOD AND SYSTEM FOR TESTING SURFACES FOR CONTAMINANTS

RELATED APPLICATION

This application claims the priority benefit of U.S. Provisional Application No. 62/306,369, filed Mar. 10, 2016, for "Method and System for Testing Surfaces for Contaminants" by Leon Vandervalk et al., the entirety of which is incorporated by reference.

FIELD

The present invention pertains to testing surfaces in the field. More particularly, the present invention concerns methods and systems for testing surfaces for contaminants such as soluble salts prior to applying a protective coating onto a particular surface.

BACKGROUND

It is known in the art that prior to the application of protective coatings on a surface, it is necessary to determine if the surface is free of contaminants, and in particular, soluble salt contaminants. Contaminants that are not removed prior to the application of a protective coating can lead to the failure of the protective coating and corrosion of the surface to be protected. For example, soluble salts on a metal surface can cause adhesion problems due to the hygroscopic nature of salt which attracts water through the permeable protective coating, resulting in a build-up of water molecules between the surface and the coating. This results in the creation of osmotic pressure, the creation of an electrolytic cell, and ultimately causes corrosion of the surface. It is particularly important to determine if soluble salt contaminants exist on the surface so that attempts to clean the surface before coating do not inadvertently embed contaminants into the surface material. Furthermore, performance standards for protective coatings typically define the allowable concentration of soluble salts so it is important to determine the concentration of such salts on the surface prior to application of the protective coating.

To test for the presence of contaminants, chemical reaction tests that provide colored indications as to the concentration of soluble solvents in a solution have been devised, along with conductivity measurement tests. Multiple techniques for collecting samples from a surface have also been developed including swabbing, boiling, using a test sleeve, and using as Bresle patch.

Swabbing relies on using a cotton swab soaked in a measured amount of solution. A measured area of the contaminated surface is brushed with a damp cotton swab. The damp cotton swab is swirled in the solution and squeezed. This process is repeated several times with new cotton swabs, and each time the cotton swabs are left in the solution. Finally, a fresh cotton swab is then used to dry the surface and is also deposited in the solution. The solution with the cotton swabs is stirred for several minutes, and the concentration of salt is then measured. The disadvantage of the swabbing method is that it is labor intensive, and subject to contamination from the swabs, the user's hands, and tweezers used for swabbing. The measurement may also be inaccurate due to a failure to retain all of the test solution, especially on sloped or overhead surfaces.

Boiling involves taking a sample of the contaminated surface into a laboratory and boiling it in a measured volume of deionized water for one hour. The concentration of salt in the test solution is then measured. The involvement of the laboratory is a disadvantage of this method, as is the requirement that a sample of the surface must be removed from the job site. Like the swiping method, contamination is possible, either from prior tests or from contaminations in the boiled water.

The test sleeve method involves a cylindrical latex sleeve with a dosed end and an open end with an adhesive ring. The test sleeve is filled with a measured amount of water which collects at the closed end of the sleeve. The adhesive ring at the open end of the sleeve is then placed in contact with the surface to be measured, and the closed end of the sleeve is raised. The measured amount of water flows to the open end of the sleeve and makes contact with the surface to be measured. The test sleeve is then agitated to help the water dissolve the contaminants on the surface. The closed end is then lowered to allow the solution to flow as from the surface at the open end of the test sleeve. The sleeve is then removed from the surface and the solution measured. This method is difficult to employ on horizontal surfaces since gravity pulls the solution towards the open end of the test sleeve, complicating removal of the sleeve and retention of the test solution. It can also be difficult to remove the solution from the test sleeve after it has been removed from the surface.

The Bresle patch method starts with a dry portion of the metallic surface with no rust, dirt, or moisture so that a patch frame with an adhesive may be applied to the metallic surface. The Bresle patch is then applied onto the metallic surface with adhesive to form a tight seal. Typically, the patch is a latex sheet with a double-sided adhesive foam ring on one side. A sampling chamber is formed between the latex and the metallic surface enclosed by the foam ring. Ideally, the Bresle patch will be applied in a manner so that little air is sealed within the patch. The characteristics of a certain amount of deionized water are then measured prior to injection into the Bresle patch so that a baseline may be established. This same amount of deionized water is then injected into the Bresle patch and agitated by the user so that any soluble salts on the metallic surface are dissolved in the deionized water. Typically, the latex sheet accommodates the injected deionized water through its elasticity. The deionized water may also be removed and reinjected into the Bresle patch to further dissolve any soluble salts. The deionized water is then collected from the Bresle patch and measured. The difference between the second and first measured value represents the level of contamination on the surface.

Although the Bresle method is popular, there are disadvantages. The patch used in the Bresle method relies on an adhesive to attach to the surface to be measured. This adhesive can fail to create a watertight seal in situations where, for example, the surface is heavily pitted, the surface has been blasted by particles in an attempt to clean the surface, and the surface is curved. The adhesive can also leave behind a residue, further contaminating the surface. The patches may also contain contaminants and therefore distort measurements. The single-use nature of the patches generates waste and increases the cost of the test. The requirement for a needle is another disadvantage associated with the Bresle method. A sharp needle capable of piercing the latex and the foam adhesive of the patch is also capable of injuring the user. On some job sites, the sharp needle is sufficient to complicate or limit the adoption of the Bresle method. The process of penetrating through the latex and adhesive foam while maintaining a watertight seal can also be challenging. The need to measure samples of the water both before and after injection into the patch complicates this method as well, and also creates an additional opportunity for contamination. It is also necessary to remove all of the water deposited into a conductivity meter during the pre-measurement reading or the amount of water injected into the patch may be incorrect. Other steps that are typically performed may also provide opportunities for contamination. For example, users will often meter out more water than is necessary into the syringe, and inject some of this water into the conductivity meter prior to pre-measurement. The water is then discarded from the meter and from the syringe until the syringe has the desired volume. This additional step that is not strictly necessary to the performance of the Bresle method introduces the opportunity for contamination if the conductivity meter is not properly cleaned.

These and other deficiencies in known methods of testing for contaminants on a surface are addressed by the method and system described here.

SUMMARY OF THE INVENTION

The system described here includes an apparatus for facilitating testing a surface for contaminants with an air-permeable water-resistant membrane, an overlay with overhangs configured to apply pressure onto a complementary surface, and a test chamber configured with the complementary surface for receiving pressure applied by the overlay. The test chamber defines a void of a particular volume formed between the test chamber and the surface. The overlay and the test chamber include orifices that align to define a path from an external wall of the overlay to an internal wall of the test chamber.

The method described here includes assembling the device, inserting a dispensing tube along the path from the external wall of the overlay to the internal wall of the test chamber, depositing a predetermined amount of solvent into the void of the test chamber, agitating the predetermined amount of solvent in the void of the test chamber, retrieving substantially all of the predetermined amount of solvent from the void of the test chamber, and characterizing the properties of the solvent to derive a level of contamination of the surface.

The system, apparatus, and described here removes the need for adhesives and sharp objects, is reusable, and reduces the number of steps necessary to test a surface for contaminants.

BRIEF DESCRIPTION OF THE DRAWING FIGURES

DETAILED DESCRIPTION OF THE INVENTION

The system and method described here allows for the testing of surfaces for contaminants such as soluble salts. One way this is done by utilizing the testing apparatus described here. By including the testing apparatus in a test kit for testing substrates, various disadvantages in known techniques for testing surfaces can be avoided.

Figure 1:
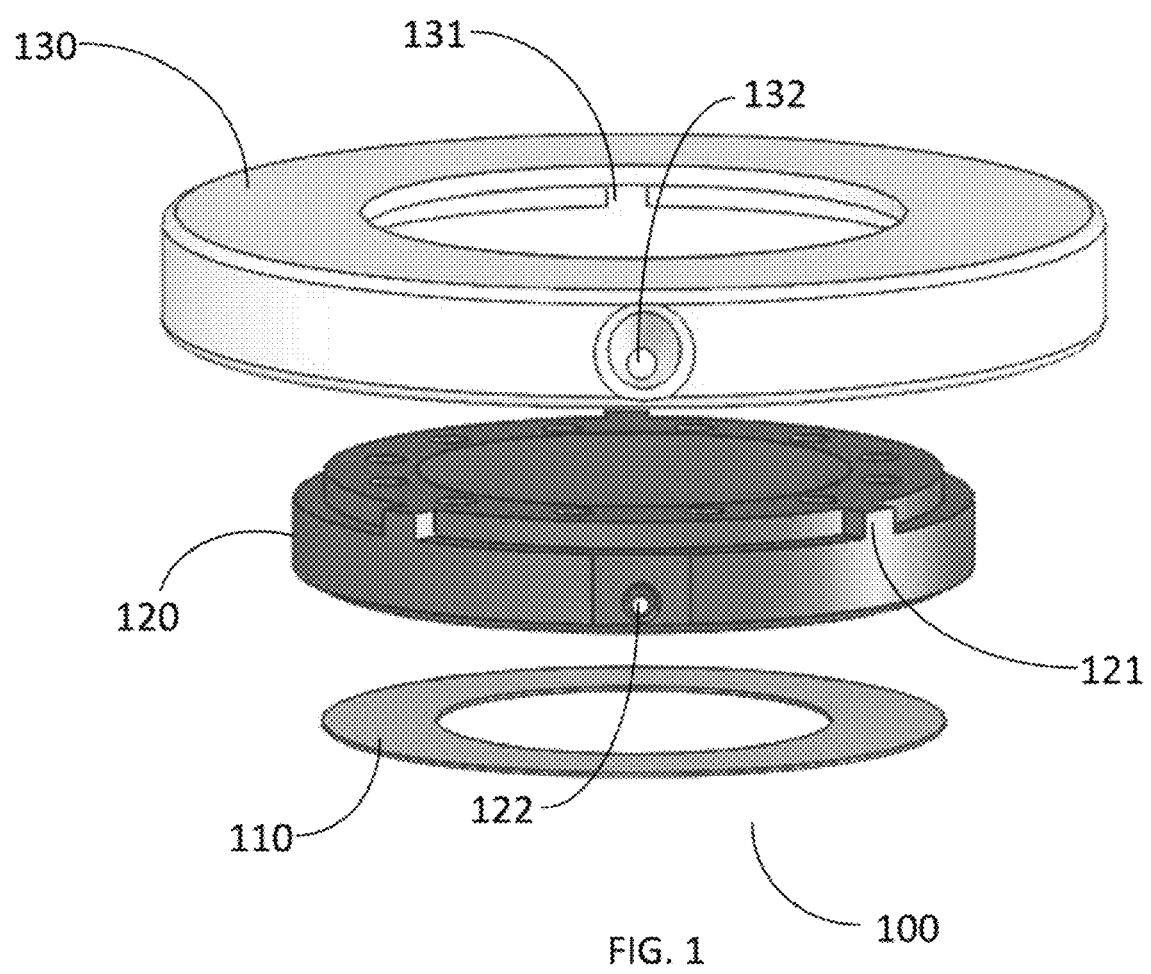
FIG. 1 depicts an exploded view of art embodiment of the apparatus for creating a test chamber on a surface.

FIG. 1 depicts components of one embodiment of the testing apparatus 100 in an exploded fashion to show an air-permeable water-resistant membrane 110, a test chamber 120, and an overlay 130. Each of the components cooperate with one another to form the embodiment of the complete testing apparatus 100 which facilitates testing of substrates. As shown in the drawings, this embodiment of the testing apparatus 100 includes alignment features 121 that exist on the test chamber 120 and alignment features 131 that exist on the overlay 130 so that features of the test chamber 120 may be appropriately oriented in relation to features of the overlay 130. One example of such a feature requiring such appropriate orientation is the orifice 122 formed on the test chamber 120 and the orifice 132 formed in the overlay 130. Other features may also exist to facilitate alignment of the components of the testing apparatus 100 but are not specifically depicted.

The overlay 130 of this embodiment of the testing apparatus 100 is formed of metal or another rigid or semi-rigid material. Although these are just examples, it should be noted that any material may be used so long as the material itself can apply the needed pressure to secure the testing apparatus 100 to the surface to be tested without deforming or otherwise becoming damaged. As shown in the drawings, the overlay 130 has an annular or ring shape for placement over the flange 123 of a similarly shaped test chamber 120. The overlay 130 defines a void into which the dome 124 of the test chamber 120 extends. The overlay 130 is configured to apply pressure onto a surface of the test chamber 120, to be described below. This pressure is sufficient to form a water-tight seal between the testing apparatus 100 and the surface being tested.

Figure 4:
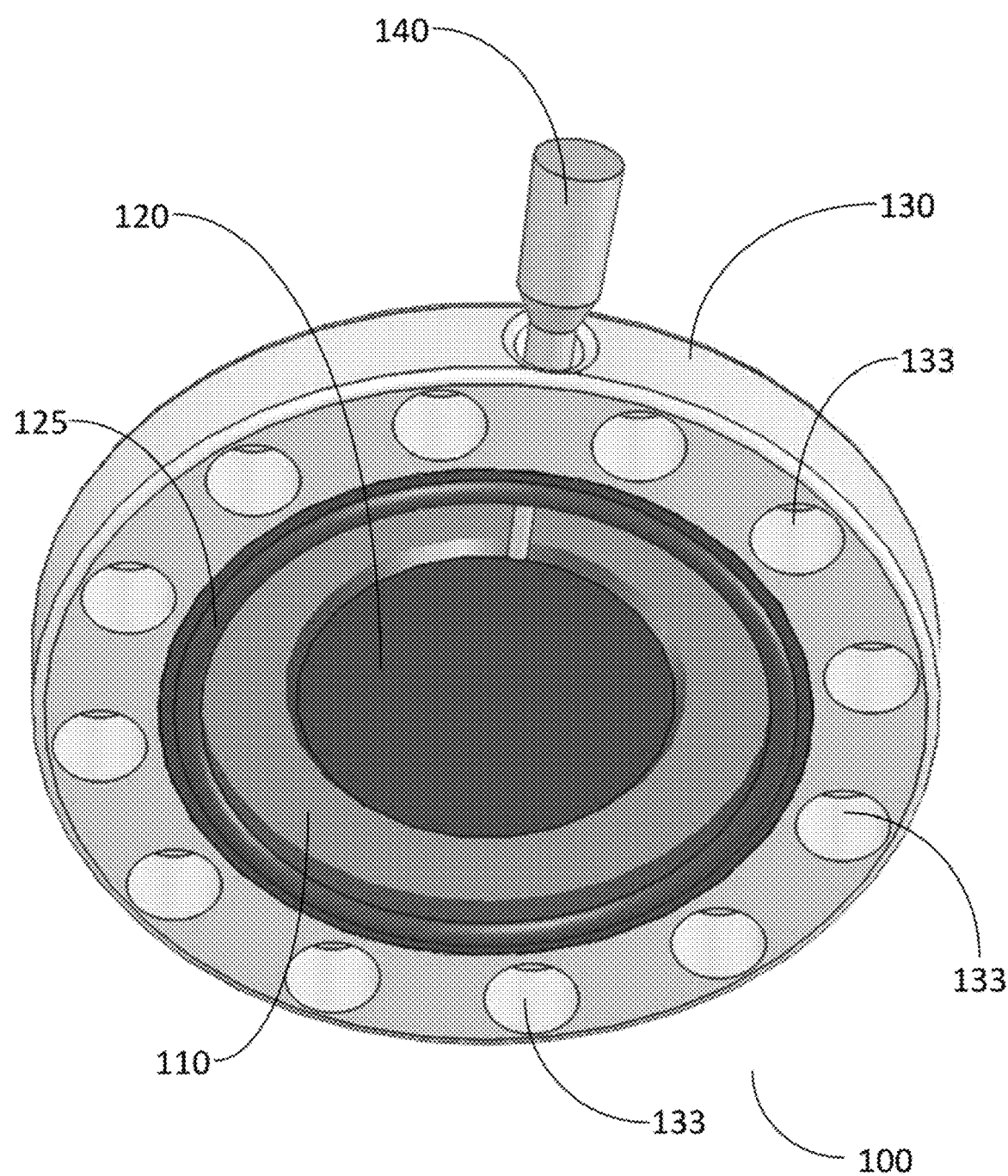
FIG. 4 depicts a bottom view of the apparatus.

One way this pressure is generated is through the use of a continuous magnet or a plurality of magnets on a bottom surface of the overlay 130 so that the overlay 130 is attracted to come into direct contact with ferromagnetic surfaces. In some embodiments, the magnet or magnets may be encased by the overlay 130 so that direct contact with the metallic surface is not possible. In such an embodiment, the encasing material does not significantly interfere with the magnetic forces being supplied by the magnets. FIG. 4 depicts one embodiment where a plurality of magnets 133 is employed to secure the overlay 130 onto the metallic surface. By virtue of the magnetic force generated by the magnets 133 of the overlay 130, pressure is applied onto the flange 123 of the test chamber 120 so that an appropriate seal between the test chamber 120 and the gasket 125 and the surface to be tested is formed. The amount of magnetic force supplied by the overlay 130 should be sufficient to reliably form an appropriate seal between the test chamber 120 and the surface to be tested. In some embodiments, the amount of magnetic force supplied by the overlay 130 may be adjustable by increasing or decreasing the number, the size, or the type of magnets held by the overlay 130. In other embodiments, the overlay 130 is tailored to provide a particular amount of magnetic force on a particular type of metallic surface.

Other techniques of generating this pressure are also possible. For example, the overlay 130 may be formed so that an adhesive may be applied onto a bottom surface of the overlay 130. This adhesive is of sufficient strength to securely attach the overlay 130 onto the surface, and of sufficient strength to also apply the desired pressure onto the testing chamber 120 so that a water-tight seal between the testing apparatus 100 and the surface is formed. In another example, an overlay 130 formed of metal is magnetically attracted to a particular surface through the use of a separate magnet. In this example, the overlay 130 is on one side of the surface to be tested, and a magnetic force originates from the opposite side of the surface so that sufficient pressure is applied onto a surface of the test chamber 120. In this embodiment, the overlay 130 does not provide the forces needed to generate the pressure on the test chamber 120. Rather, an external magnet provides the needed forces to generate the desired pressure. Other techniques for generating the desired pressure are also contemplated but not specifically enumerated here.

In addition to providing the pressure necessary to form an appropriate seal between the test chamber 120 and the surface, the overlay 130 may also include aspects that help facilitate the removal of the testing apparatus 100 from the surface. In some embodiments, an upper surface of the overlay 130 may extend radially outward to form a tab that facilitates removal of the overlay 130 from the surface. In other embodiments, only a portion of the upper surface of the overlay 130 extends radially outward to form at least one tab to facilitate removal of the overlay 130 from the surface. For certain embodiments it may be preferable to rely on a separate tool to facilitate removal of the testing apparatus 100. In these embodiments, a notch may exist on the outer circumferential surface of the overlay 130 so that the tool may apply the necessary force to overcome the forces securing the testing apparatus 100 to the surface. Other structural features to facilitate the removal of at least the overlay 130 are contemplated by not specifically described here.

Figure 2:
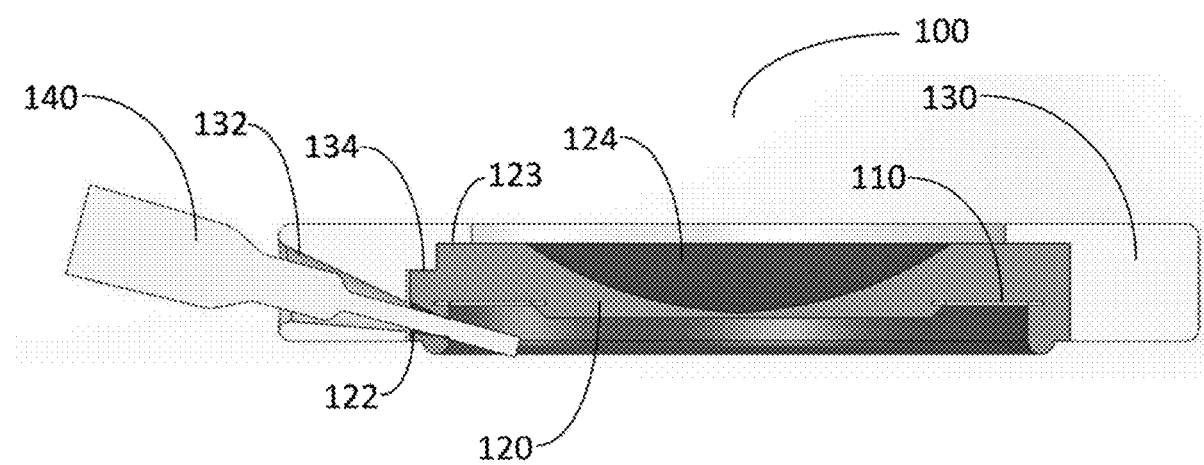
FIG. 2 depicts a cross-sectional view of the apparatus.
Figure 3:
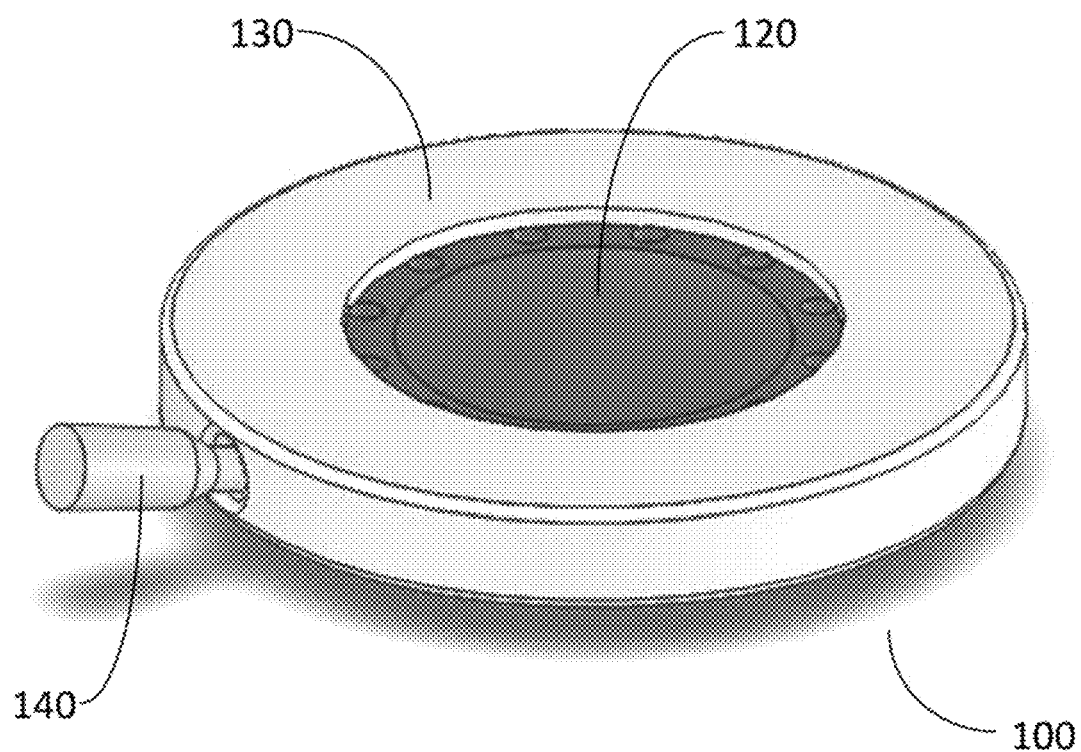
FIG. 3 depicts a top view of the apparatus.

As shown in, for example, FIG. 2, an overhang 134 is formed in the overlay 130 to apply pressure onto the complementary flange 123 of the test chamber 120 so that a seal is formed between the test chamber 120 and the surface. Certain portions of the overlay 130 may include multiple overhangs 134 to apply pressure onto complementary flanges 123 of the test chamber 120 to help ensure the seal between the test chamber 120 and the surface is appropriate. Portions of the flanges 123 and the overhangs 134 may be aspects of the alignment features 121, 131 of the testing chamber 120 and the overlay 130, respectively.

The overlay 130 also includes an orifice 132 that is formed to penetrate from an outer wall to an inner wall of the overlay 130. The orifice 132 shown in the drawings is dimensioned to allow for easy insertion and removal of a dispensing tube 140. In some embodiments, as shown in FIG. 2, the orifice 132 tapers in a manner that helps guide the dispensing tube 140 to a corresponding orifice 122 of the test chamber 120, described below. By including this tapering, the user need not precisely align the dispensing tube with the orifices 122, 132 which helps improve usability and facilitate testing of the surface. Other features such as grooves or slots may also be employed to facilitate guiding of the dispensing tube to the orifice 122 of the test chamber 120.

The test chamber 120 is configured to interface with the overlay 130 at various points. For example, FIG. 2 depicts how the flanges 123 of the test chamber complement overhangs 134 of the overlay 130 so that pressure may be applied onto the test chamber 120 to ensure that an appropriate seal is formed between the test chamber 20 and the surface. Multiple flanges 123 may exist on at least portions of the test chamber 120 to help align the components of the testing apparatus 100 while also providing surfaces onto which pressure may be applied. In addition, the alignment features 121 of the test chamber 120 shown in FIG. 1 may also provide appropriate surfaces onto which pressure may be applied by the overlay 130. The test chamber 120 may be made of any appropriate material including plastics, silicones, or other resilient materials. In some embodiments, the test chamber 120 may be formed of a translucent material to allow a user to determine the levels of fluid contained within. In certain embodiments, the test chamber 120 may be formed of materials to facilitate reuse in a manner that avoids cross-contamination between tests. In other embodiments, the test chamber 120 has been designed for a single use to minimize the possibility of contamination.

The test chamber 120 defines a void into which deionized water may be injected and removed through the orifice 122. The void is circumferentially enclosed by the rigid structure of the test chamber 120, and is further enclosed by a flexible material formed in a dome or dome-like shape 124. By incorporating the dome 124 in the test chamber 120, variations in the amount of solution injected into the test chamber 120 need not be precisely measured. Rather, in the event that excess solution is injected in the test chamber 120, the dome 124 helps accommodate the excess solution without causing leakage from the test device 100 through, for example, the air-permeable water-resistant membrane 110 described below. In addition, the dome 124 may be used to agitate the solution injected into the test chamber 120 so that any soluble salts on the surface being tested are collected. The dome 124 may be integrally formed with the structure of the test chamber 120 to further prevent leakage along the circumferential edge of the dome 124, for example. Although the dome 124 of the test chamber 120 is depicted in a hemispherical shape in, for example, FIG. 2, this structure 124 need not be formed in this shape. Embodiments that instead merely use a thin or deformable material to accommodate excess solution without causing leakage from the test device 100 are contemplated, but are not specifically enumerated here. Further, the structure 124 need not be made of the same material as other aspects of the test chamber 120.

The test chamber 120 also includes an air-permeable water-resistant membrane 110 that allows for atmospheric gases to escape from the void of the test chamber 120. In some configurations shown in FIGS. 1, 2, 4, the air-permeable water-resistant membrane 110 circumferentially surrounds the dome 124 of the test chamber 120. The air-permeable water-resistant membrane 110 allows for any atmospheric gases captured in the void to be evacuated from the void so that a more accurate measurement may be obtained. In some embodiments, the air-permeable water-resistant membrane 110 is attached to the test chamber using an adhesive to provide a water-tight seal. This water-tight seal is necessary so that no portion of the solution injected into the test chamber 120 is lost. Other structural features may be utilized instead of the membrane 110 such as one-way valves so long as the atmospheric gases contained in the void may be evacuated but are not specifically described here.

In some embodiments of the test chamber 120 as shown in FIGS. 2, 4, a gasket 125 is included which helps facilitate the formation of a seal between the test chamber 120 and the surface. The gasket 125 may be made of any suitable material including rubber or elastomers. In some embodiments, the gasket 125 is an O-ring. When the pressure from the overlay 130 is applied to the test chamber 120, the gasket 125 deforms to help ensure a proper seal is formed to isolate a void formed between a void in the test chamber 120 and the surface. The gasket 125 may be integrally formed with the structure of the test chamber 120 to prevent leakage. In some embodiments, the gasket 125 may be replaceable after repeated use.

The orifice 122 of the test chamber 120 is aligned with the orifice 132 of the overlay 130 thanks to the structural configuration of the alignment features 121, 131 which guarantees the proper alignment of the orifices 122, 132. As described above, the orifice 132 of the overlay 130 includes structural features that help align a dispensing tube 140 so that insertion through the orifice 132 of overlay 130 and the orifice 122 of the test chamber 120 is facilitated. In some embodiments, the orifice 122 of the test chamber 120 includes a one-way valve or other reusable structural device that ensures the contents of the void of the test chamber 120 do not escape.

For example, in one embodiment the orifice 122 of the test chamber 120 includes at least two walls that cooperate to seal liquid and other material contained in the void of the test chamber 120. This type of a seal may be referred to as a "duckbill" one-way valve. When a user inserts a dispensing tube 140 into the orifice 122 of the test chamber, a tip of the dispensing tube 140 contacts the point of intersection of the at least two walls. As the user continues to insert the dispensing tube 140 into the orifice 122 of the test chamber 120, the at least two walls separate from one another so that the dispensing time 140 may access the void of the test chamber 120. In some embodiments, the at least two walls have elasticity which allows for the walls to come together after the dispensing tube 140 is removed so that the void of the test chamber 120 is resealed.

In another embodiment, the orifice 122 of the test chamber 120 is instead sealed by an O-ring arranged to provide a seal sufficient to retain the solution within the test chamber but also sufficiently deformable so that the tip of a dispensing tube 140 may displace the O-ring so that solution may be injected and removed from the test chamber 120. This O-ring may, in some embodiments, be a structure that is integrally molded as part of the test chamber. In other embodiments, the orifice 122 includes a single-use structural device for ensuring the contents of the void of the test chamber 120 do not escape. Such a single-use structural device may include a perforatable material that can be perforated by the tip of the dispensing tube 140.

As described above, the test apparatus 100 helps improve the efficiency of testing for soluble salts and other contaminants on a surface by facilitating the creation of a watertight chamber where soluble salts present on the surface being tested are dissolved into the solution injected into the test chamber 120 by the dispensing tube 140, and then be extracted from the test chamber 120. The dispensing tube 140, containing the solution to be tested, is then removed from the orifices 122, 132 of the testing apparatus 100 and the contained solution deposited and tested for conductivity, among other properties. It is also possible to employ a device that incorporates the components needed to test for the presence of soluble salts or other contaminants in the solvent. More particularly, dispensing tube 140 may be incorporated into a smart syringe which allows for the injection and removal of solution, and also allows for testing the properties of the removed solution without requiring a separate testing device. In one embodiment of the smart syringe, a separate chamber retains at least some of the solution for testing. In another embodiment, the entirety of the solution contained in the smart syringe is utilized for testing. In either of these embodiments, portion or entirety of the solution may be tested both prior to and after injection into the test chamber 120. Thus, in addition to simplifying the testing process, the smart syringe also helps reduce the possibility for inadvertent contamination. In addition to performing conductivity testing, the smart syringe may precisely meter the amount of solution that is injected and removed from the testing apparatus 100 to help improve the repeatability of the tests.

A method of performing a test using one embodiment of the testing apparatus 100 involves placement of the test chamber 120 against a chosen surface. In some embodiments, placement of the air-permeable water-resistant membrane 110 occurs prior to placement of the test chamber 120. The overlay 130 is then placed on top of the test chamber 120 and alignment features 131, 121 are used to ensure proper placement. The pressure provided by the overlay 130 ensures an appropriate seal is formed between the test chamber 120 and the surface. The user then uses a dispensing tube 140 to deposit liquid into the void within the test chamber 120. Certain embodiments of this method may include testing of the characteristics of the liquid prior to deposit in the void of the test chamber 120. The dispensing tube 140 may be attached to a syringe or other device which includes graduations or other markings to indicate the appropriate amount of liquid to be collected and dispensed through the dispensing tube 140 into the void of the test chamber 120. The liquid may be at least partially repeatedly collected and dispensed to help mix the liquid with any contaminants on the surface being tested. The liquid may then be from the void of the test chamber 120 and the characteristics of the liquid then compared against the results of prior test or a control test. In some embodiments of this method, the dispensing tube may include the ability to test the characteristics of the liquid without requiring the removal of the liquid from the void of the test chamber 120.

Figure 5A:
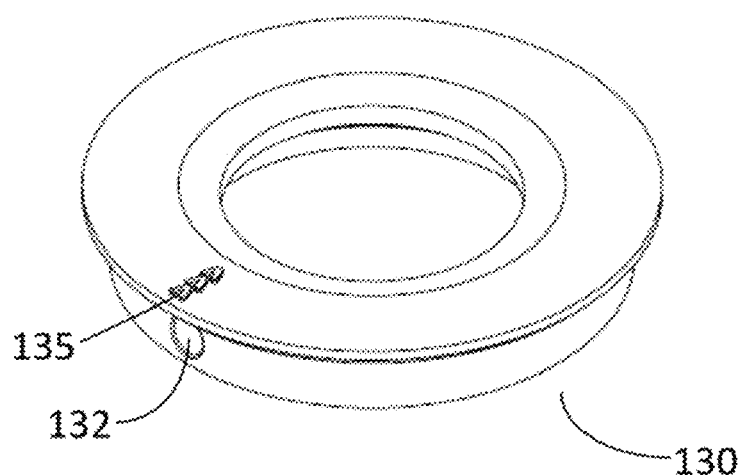
FIGS. 5A, 5B depict views of the embodiments of the overlay of the apparatus.

FIG. 5A depicts a top view of an embodiment of an overlay 130 used with the testing apparatus 100 so that a surface can be tested for contaminants. As shown in FIG. 5, this embodiment of the overlay 130 includes an orifice 132 that penetrates from an outer wall to an inner wall of the overlay 130. In addition, the embodiment of the overlay 130 shown in FIG. 5 includes indicia 135 on a surface of the overlay 130. In some embodiments, a variety of indicia 135 may provide branding or marketing information, and in still further embodiments the indicia 135 may provide information to the user. In certain embodiments, the indicia 135 may include tactile aspects such as raised or lowered features that can be identified by the user through touch. The embodiment of the overlay 130 shown in FIG. 5A includes such tactile indicia 135 that provides information to the user such as orientation of the overlay 130 and the position of an orifice 132 formed in the overlay 130 by virtue of the placement of the tactile indicia 135 relative to the orifice 132. Such tactile indicia 135 that provide orientation information for the components of the testing apparatus 100 may be particularly useful for situations when the user must test multiple surfaces or multiple areas of the same surface repeatedly. Other arrangements of indicia 135 relative to other features of the overlay 130 are possible and not specifically depicted and described here. The indicia 135, in combination with other aspects of the testing apparatus 100, help ensure the user properly employs the testing apparatus 100 so that the surface can be properly tested for contaminants.

Figure 5B:
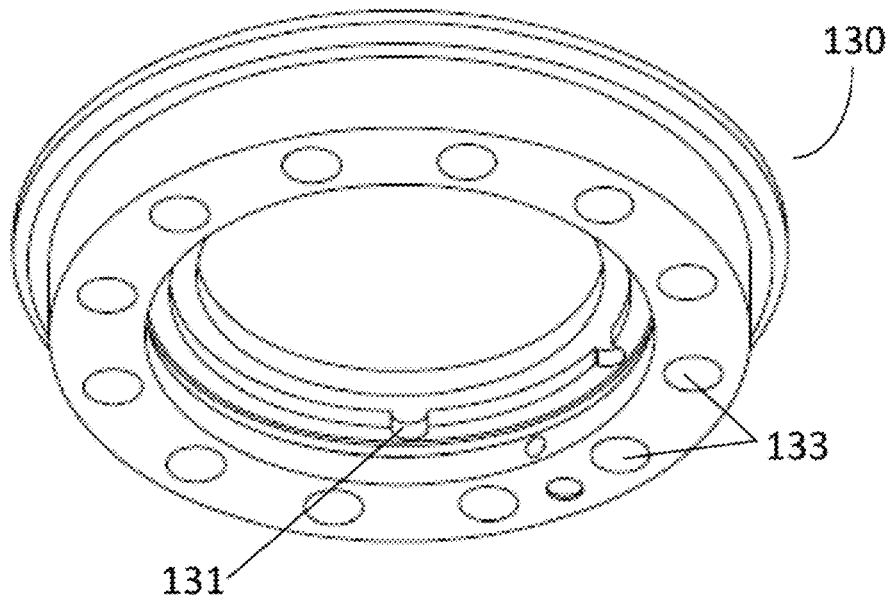

FIG. 5B depicts the bottom view of the overlay 130 shown in FIG. 5A. The bottom view of the overlay 130 depicts the multiple alignment features 131 formed in the overlay 130. The alignment features 131 depicted in FIG. 5B may, in some embodiments, cooperate with alignment features 121 located on a test chamber 120 so that the testing apparatus 100 is easily assembled by the user. FIG. 5B also depicts the plurality of magnets 133 that are included with the embodiment of the overlay 130. As shown in FIG. 5B, the magnets 133 may be distributed at the perimeter of the overlay 130 to provide approximately even pressure onto the test chamber 120. In other embodiments, the magnets 133 may be distributed in any appropriate manner so that the appropriate pressure is provided onto the test chamber 120. In still other embodiments, magnets 133 with different properties include different sizes, shapes, and strengths, may be used in combination as long as the appropriate pressure is applied onto the test chamber 120. For example, the magnets 133 may be formed in a cone shape, a T-shape, an X-shape, or other shape that provides the desired magnetic force. In certain embodiments, the magnets 133 may be arranged in a manner so that more pressure is provided near the orifice 132 of the overlay 130. Other modifications regarding the number and distribution of the magnets 133 are contemplated but not explicitly enumerated here.

The above described testing apparatus 100 and method for performing a test using the testing apparatus 100 is suited for a variety of surfaces with different coatings, but is particularly suited for surfaces that are substantially planar. Such substantially planar surfaces may include, for example, floors, walls, or other similar structures. It is, however, also desirable to test other surfaces that are not substantially planar for contaminants.

Figure 6A:
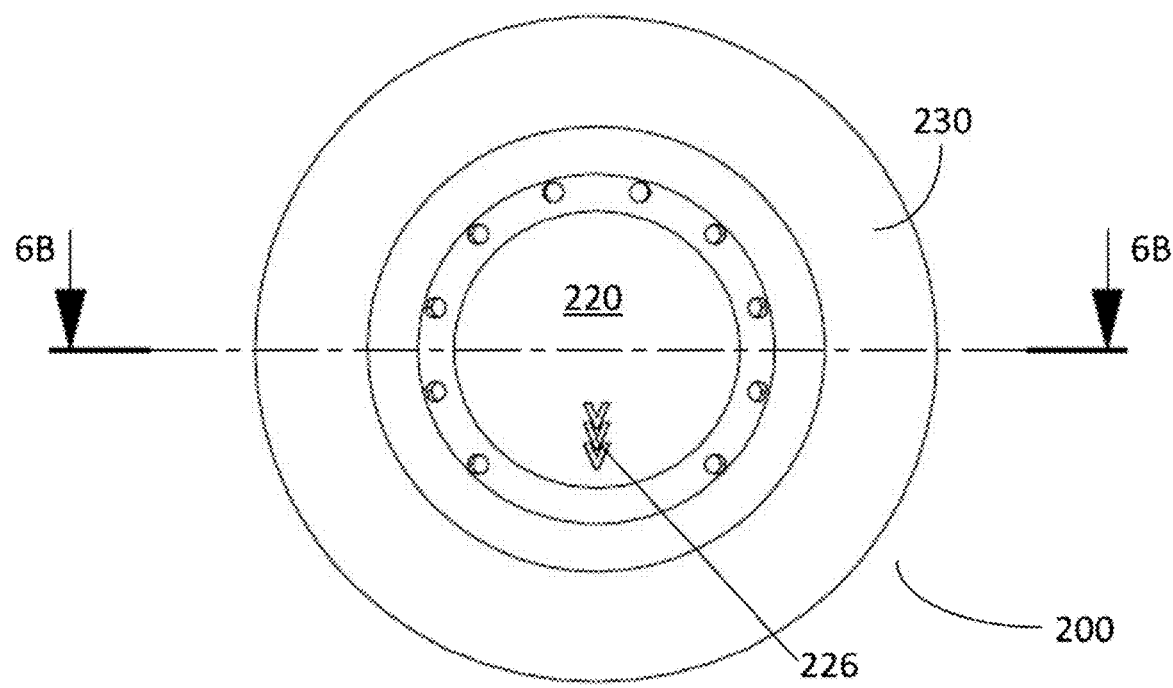
FIGS. 6A, 6B depict views of another embodiment of the apparatus for creating a test chamber on a surface.
Figure 6B:
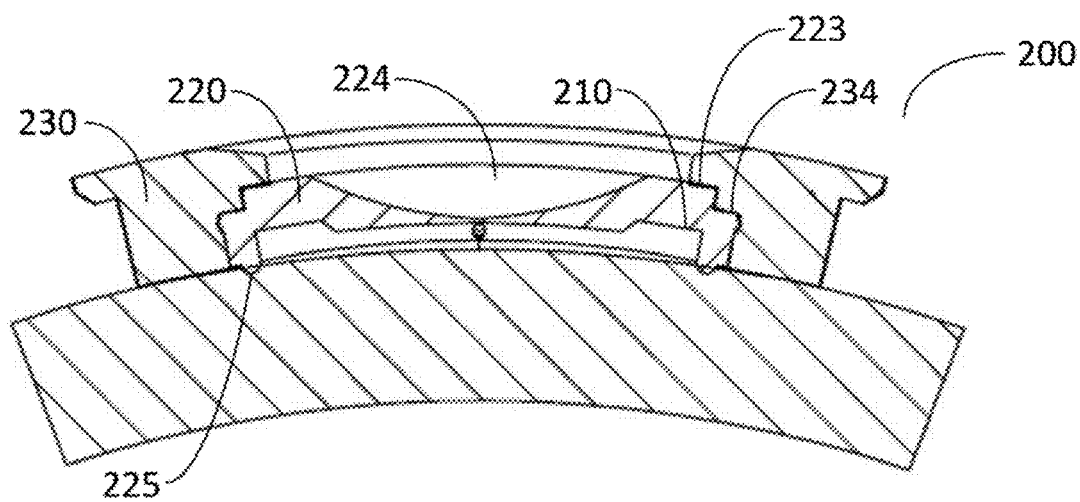

Accordingly, another embodiment of the testing apparatus 200 is configured to test surfaces that are curved either inwardly or outwardly. Such a testing apparatus 200 includes, among other aspects, an overlay 230 that can deform and continue to provide the desired pressure so that the testing chamber 220 can be used to test the curved surface for contaminants. In such embodiments of the testing apparatus 200, the testing chamber 220 also deforms so that the curved surface can be tested for contaminants as easily as a substantially planar surface can be tested for contaminants. Such a deformable overlay 230 is shown in FIGS. 6A, 6B.

Specifically, the flexible testing apparatus 200 embodiment includes an overlay 230 that can deform to conform to both inwardly or outwardly curved surfaces so that the desired pressure on the testing chamber 220 can be applied so that the inwardly or outwardly curved surfaces can be tested for contaminants. Such a flexible overlay 230 is made of an appropriate material such as silicone, rubbers, plastics, and other materials that can apply the needed pressure to secure the testing apparatus 200 to the surface to be tested without deforming or otherwise becoming damaged. Like the overlay 130, the overlay 230 described here has an annular or ring shape for placement over a test chamber 220. In the depicted embodiment, the overlay 230 defines the void into which the dome 224 of the test chamber 220 extends. The flexible overlay 230 is configured to apply pressure onto the surface of the test chamber 220 so that a water-tight seal is formed between the testing apparatus 200 and the surface being tested.

Like the previously described overlay 130, one way the flexible overlay 230 generates this pressure is through the use of a continuous magnet or a plurality of magnets on a bottom surface of the overlay 230 so that the overlay 230 is attracted to come into direct contact with ferromagnetic surfaces. The magnets may, in some embodiments, be coated with materials that provide a surface that results in a bond that appropriately retains the magnets 133, 233 in desired portions of the overlay 130, 230. In still other embodiments, the magnets may be entirely encased by the flexible overlay 230 to protect the magnets from environmental elements and to ensure the magnets are retained in appropriate positions. By virtue of the magnetic force generated by the magnets of the overlay 230, pressure is applied so that an appropriate seal between the test chamber and the surface to be tested is formed. The amount of magnetic force supplied by the overlay 230 should be sufficient to reliably form an appropriate seal between the test chamber 220 and the surface to be tested. In some embodiments the amount of magnetic force supplied by the overlay 230 may be adjustable by increasing or decreasing the number, the size, or the type of magnets held by the overlay 230. In other embodiments, the overlay 230 is tailored to provide a particular amount of magnetic force on a particular type of metallic surface.

Like the previously described overlay 130, the flexible overlay 230 may include aspects that facilitate the removal of the testing apparatus 200 from the surface. In some embodiments, an upper surface of the overlay 230 may extend radially outward to form a tab that facilitates removal of the overlay 230 from the surface. In other embodiments, only a portion of the upper surface of the overlay 230 extends radially outward to form at least of tab to facilitate removal of the overlay 230 from the Surface. It is also possible that in some embodiments, portions of the flexible overlay 230 are strengthened so that removal using the strengthened portion of the flexible overlay 230 is facilitated. For certain embodiments it may be preferable to rely on a separate tool to facilitate removal of the testing apparatus 200. In these embodiments, a notch may exist on the outer circumferential surface of the overlay 230 so that the tool may apply the necessary force to overcome the forces securing the testing apparatus 200 to the surface. Other structural features to facilitate the removal of at least the overlay 230 are contemplated by not specifically described here.

The flexible overlay 230 also includes structural features to apply pressure on complementary features of the test chamber 220. For example, FIG. 6B illustrates how an overhang 234 is formed in the overlay 230 to apply pressure onto the complementary flange 223 of the test chamber 220 so that a seal is formed between the test chamber 220 and the surface. Certain portions of the flexible overlay 230 may include multiple overhangs 234 to apply pressure onto complementary flanges 223 of the test chamber 220 to help ensure the seal between the test chamber 220 and the surface is appropriate. Portions of the flanges 223 and the overhangs 234 may be aspects of the alignment features 221, 231 of the testing chamber 220 and the overlay 230 respectively. In some embodiments of the flexible overlay 230, portions that apply pressure onto the test chamber 220 may be reinforced in a manner that facilitates the creation of the water-tight seal between the test chamber 220 and the surface being tested.

The flexible overlay 230 also includes an orifice 232 formed to penetrate from an outer wall to an inner wall of the overlay 230. The orifice 232 is dimensioned for easy insertion and removal of a dispensing tube 140. Similar to the embodiment depicted in FIG. 2, for example, the orifice 232 may taper in a manner that helps guide the dispensing tube 140 to a corresponding orifice 222 of the test chamber 220. By including this tapering, the user need not precisely align the dispensing tube with the orifices 222, 232 which helps improve usability and facilitate testing of the surface. Other features such as grooves or slots may also be employed to facilitate guiding of the dispensing tube 140 to the orifice 222 of the test chamber 220. Additionally, embodiments of the flexible overlay 230 may employ different materials for at least a portion of the orifice 230 so that the dispensing tube 140 is appropriately guided to the corresponding orifice 222 of the test chamber 220.

The flexible overlay 230 in FIG. 6A is shown with a test chamber 220 inserted so that testing of the curved surface may proceed. The test chamber 220 shown in FIG. 6A includes indicia 226 that provides information to the user such as orientation of the test chamber 220. Such indicia 226 may be tactile and provide orientation information for the components of the testing apparatus 100 may be particularly useful for situations when the user must test multiple surfaces or multiple areas of the same surface repeatedly. For example, the indicia 226 may indicate the location of an orifice 222 of the test chamber 220 that aligns with the orifice 232 of the overlay 230 so that a dispensing tube 140 may be used described above. Other arrangements of indicia 226 relative to other features of the testing chamber 220 are possible and not specifically depicted and described here. The indicia 226, in combination with other aspects of the testing apparatus 200, help ensure the user properly employs the testing apparatus 200 so that the surface can be properly tested for contaminants.

FIG. 6B illustrates a cross-section of the flexible testing, apparatus 200 shown in FIG. 6A. FIG. 6B depicts how the testing apparatus 200 deforms so that testing of the curved surface for contaminants is possible. In particular, the test chamber 220 is deformed and held against the curved surface at least in part by the pressure being applied by the flexible overlay 230. As shown in the cross-section, the components of the test chamber 220 and the flexible overlay 230 cooperate so that testing of the curved surface is possible. Specifically, the various features of the test chamber 220 including the flange 223 cooperate with the various features of the flexible overlay 230 including the overhang 235. Multiple flanges 223 may exist on at least portions of the test chamber 220 to help align the components of the testing apparatus 200 while also providing surfaces onto which pressure may be applied. Other features including the alignment features 221 of the test chamber and the alignment features 231 of the flexible overlay 230 may also cooperate to create a water-tight seal between the testing apparatus 200 and the curved surface being tested by offering surfaces onto which pressure may be applied. In addition to these aspects of the testing apparatus 200, the test chamber also includes an air permeable membrane 210, an orifice 222, and a dome 224 as described above for the embodiment of be testing apparatus 100 for testing of contaminants on substantially planar surfaces.

As shown in FIG. 6B, each of the components of the testing apparatus 200 including the test chamber 220 and the flexible overlay 230 are able to deform at substantially the same rate. In some embodiments, the test chamber 220 and the flexible overlay 230, among other components of the test apparatus 200, may have different deformation rates. For example, the test chamber 220 may be more deformable than the flexible overlay 230 so that a more appropriate seal between the test chamber 220 and the curved surface may be achieved. In other embodiments, the testing apparatus 200 may have components that are more easily deformed in one direction versus another direction. For example, the flexible overlay 230 of such an embodiment of the testing apparatus 200 may be less readily deformable when being applied to the inner diameter of a curved surface. Such an embodiment of the testing apparatus 200 may more readily deformed to conform to the outer diameter of a curved surface as shown in FIG. 6B and be less readily deformed to conform to the inner diameter of a curved surface. Such a configuration may be advantageous so that an appropriate water-tight seal is formed between the testing chamber 220 and the surface being tested. Other variances in the deformation rates of the components of the testing apparatus 200 are also possible and may be advantageous for use in certain circumstances, but are not explicitly enumerated here.

When a deformable test chamber 220 is employed, aspects of the test chamber 220 including the air-permeable water-resistant membrane 210, dome 224, and gasket 225 may also be configured to deform in a manner that preserves their function while also allowing the test chamber 220 to conform to the deformation of the flexible overlay 230. In some embodiments, alignment features 221 of the test chamber 220 deform in a manner that allows the alignment features 231 of the flexible overlay 230 to continue to cooperate and properly orient the various components of the testing apparatus 200.

Figure 7:
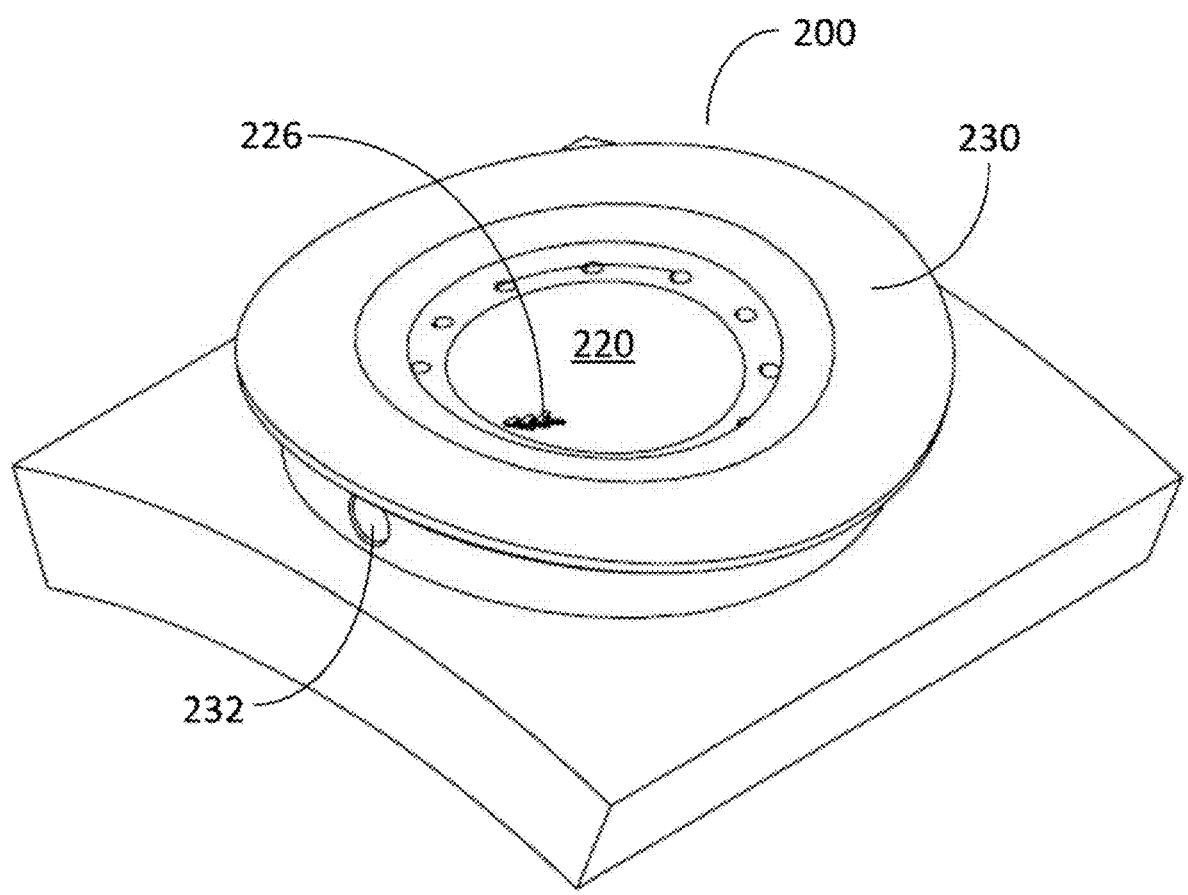
FIG. 7 depicts a perspective view of the apparatus.

FIG. 7 depicts a perspective view of the flexible test apparatus 200 as applied onto the outer diameter of a curved surface. Similar to the depictions in FIGS. 6A and 6B, the embodiment of the test apparatus 200 shown in FIG. 7 includes a test chamber 220 inserted in a flexible overlay 230 placed on the curved surface. In this depiction, the test chamber 220 includes indicia 226 that, when appropriately aligned, indicates the position of the orifice 222 of the test chamber 220 and the orifice 232 of the flexible overlay 230. Other embodiments may, however, arrange the indicia 226 on the test chamber 220 or indicia on the flexible overlay 230 at other locations to convey other types of information to the user. In the embodiment shown in FIG. 7, the indicia 226 provides at least a visual reference by which the user can quickly ascertain the orientation of the orifices 222, 232 through which the dispensing tube 140 is to be inserted. The indicia 126 may also indicate the proper assembly of the testing apparatus 200 by the consumer. In such embodiments of the testing apparatus, the orientation of the orifices 222, 232 is indicated by the indicia 226 only when the apparatus 200 is properly assembled.

Embodiments of such a flexible test apparatus 200 are suited for testing a curved inner or outer diameter of a surface for contaminants. For example, embodiments of the flexible test apparatus 200 may be employed on the inner or outer diameters of pipes having diameters ranging from about 50 inches to about 3 inches, and more particularly, diameters ranging from about 42 inches to about 4 inches. As can be appreciated, the larger the diameter of the inner or outer diameter being tested, the more similar the surface being tested is to a substantially planar surface. Thus, the embodiment of the test apparatus 200 with the flexible overlay 230 may be employed on inwardly or outwardly curved surfaces in addition to substantially planar surfaces. Such usage of an embodiment of the testing apparatus 200 on both substantially planar and curved surfaces may be particularly appropriate when the user does not have a complete understanding of the variety of surfaces that are to be tested for contaminants, such as when the user is to test the surfaces of a ship which includes both curved and substantially planar surfaces. Although the diameters of pipes were described above in relation to this embodiment of the testing apparatus 200, the apparatus 200 is not limited to the curved surfaces offered by pipes and can also be applied to other curved surfaces including portions of a ship's hull, the inner or outer walls of tanks and other curved surfaces where testing for contaminants is desirable.

Certain modifications of the above described testing apparatuses 100, 200 are contemplated. For example, in some embodiments of the apparatus, the test chamber 120, 220 and the overlay 130, 230 are integrally formed to facilitate rapid testing of surfaces. Such an embodiment may be particularly suitable when, for example, the risk of cross-contamination between the different surfaces being tested by the apparatus 100, 200 is acceptably low. In such an apparatus with integrated test chambers 120, 220 and overlays 130, 230, manufacturing of the apparatus may be facilitated, along with usage of the apparatus since only a single integral component is needed in lieu of the separate test chambers 120, 220 and overlays 130, 230. Other aspects of the separate testing chamber 120, 220 and the overlay 130, 230 will be retained in the integrated apparatus including the air-permeable water-resistant membrane 110, 210, the dome 124, 224, orifices 122, 132, 222, 232, and magnets 133, 233 will continue to perform their functions so that the water-tight seal may be established and the presence of contaminants on surfaces may be ascertained.

Although the apparatus with such an integrated test chamber 120, 220 and overlay 130, 230 may be formed of a single material, in at least some embodiments, materials with different properties in addition to different materials may be used to achieve desirable results on a variety of surfaces. In certain embodiments, although the test chamber and the overlay may be integrated components, the integrated test chamber and overlay perform the same functions in substantially the same manner as the separate test chamber 120, 220 and overlay 130, 230 described above. Additionally, certain aspects of the separate test chambers 120, 220 and the separate overlays 130, 230 may not be necessary in embodiments with integrated components including test chambers 120, 220 and overlays 130, 230. For example, in such an integrated embodiment, aspects such as alignment features 121, 221, 131, 231 may not be necessary since the components are integrated. With such an integrated construction, aspects that previously could not be ensured to be in alignment, such as the orifices 122, 222, 132, 232 of the test chamber 120, 220 and the overlay 130, 230, can be assured to be in proper orientation and alignment.

Other variations in aspects of the design of the testing apparatus 100, 200 are contemplated. In some embodiments, components of the testing apparatus 100, 200 may be coating at least partially with other materials to facilitate their use in the apparatus 100, 200.

In still further variations of the testing apparatus 100, 200, certain embodiments of the test chamber 120, 220 may include the magnets 133, 233 providing the magnetic forces needed to create a water-tight seal between the test chamber 120, 220 and the surface being tested. Such embodiments may be particularly desirable when the test chamber 120, 220 and the overlay 130, 230 are integrated components as described above. By incorporating the magnets 133, 233 into the integrated test chamber and overlay in a manner where the magnets 133, 233 are arranged in closer proximity to the sealing portions of the test chamber, a more appropriate water tight seal between the apparatus 100, 200 and the surface being tested may be achieved, particularly if the surface being tested is not substantially planar.

A method of performing a test using one embodiment of the testing apparatus 200 involves placement of the test chamber 220 against a chosen surface. The testing apparatus 200 described here includes the ability to be placed on a curved surface. In some embodiments, placement of the air-permeable water-resistant membrane 210 occurs prior to placement of the test chamber 220. A flexible overlay 230 is then placed on top of the test chamber 220 and alignment features 231, 221 are used to ensure proper placement. The pressure provided by the flexible overlay 230 ensures an appropriate seal is formed between the test chamber 220 and the curved surface. The user then uses a dispensing tube 140 to deposit liquid into the void within the test chamber 220. Certain embodiments of this method may include testing of the characteristics of the liquid prior to deposit in the void of the test chamber 220. The dispensing tube 140 may be attached to a syringe or other device which includes graduations or other markings to indicate the appropriate amount of liquid to be collected and dispensed through the dispensing tube 140 into the void of the test chamber 220. The liquid may be at least partially repeatedly collected and dispensed to help mix the liquid with any contaminants on the surface being tested. The liquid may then be extracted from the void of the test chamber 220 and the characteristics of the liquid then compared against the results of a prior test or a control test. In some embodiments of this method, the dispensing tube may include the ability to test the characteristics of the liquid without requiring the removal of the liquid from the void of the test chamber 220.

The detailed description above describes embodiments of a testing apparatus for testing a surface for contaminants, a method of testing a surface for contaminants, and a system for testing a surface for contaminants according to various embodiments disclosed here. The invention is not limited, however, to the precise embodiments and variations described. Various changes, modifications, and equivalents can be elected by one skilled in the art without departing from the spirit and scope of the invention as defined in the accompanying claims. It is expressly intended that all such changes, modifications, and equivalents which fall within the scope of the claims are embraced by the claims.

What is claimed is:

1. An apparatus for facilitating testing a surface for contaminants, the apparatus comprising:
   an overlay comprising at least one overhang configured to apply pressure onto a complementary surface of a test chamber, and an overlay orifice; and
   the test chamber comprising the complementary surface configured to receive the pressure applied by the overlay, an inner circumferential wall, an upper test chamber surface extending opposite the surface to be tested, and a test chamber orifice, the inner circumferential wall and the upper test chamber surface defining a void of a particular volume formed between the test chamber and the surface;
   wherein the overlay orifice and the test chamber orifice define a path from an external circumferential wall of the overlay to the inner circumferential wall of the test chamber.

2. The apparatus of claim 1, wherein the overlay includes alignment features configured to interface with complementary alignment features of the test chamber.

3. The apparatus of claim 1, wherein the test chamber orifice includes a one-way valve.

4. The apparatus of claim 1, wherein the test chamber orifice includes at least two surfaces that cooperate to seal liquid being held in the void of the test chamber, the at least two surfaces being separated when a tip of a dispensing tube is inserted between the two surfaces, the at least two surfaces resealing when the dispensing tube is removed from between the two surfaces.

5. The apparatus of claim 1, wherein the upper test chamber surface is configured to accommodate overfilling of the void with solvent.

6. The apparatus of claim 1, the test chamber further comprising an air-permeable water-resistant membrane.

7. The apparatus of claim 1, wherein the surface being tested for contaminants is a curved surface.

8. The apparatus of claim 1, wherein the overlay and the test chamber are integrally formed.

9. A method of testing a surface for contaminants, the method comprising:
securing the apparatus described in claim 1 to the surface;
inserting a dispensing tube along the path defined by the overlay orifice and the test chamber orifice from the external circumferential wall of the overlay to the inner circumferential wall of the test chamber;
depositing a predetermined amount of solvent into the void of the test chamber;
agitating the predetermined amount of solvent in the void of the test chamber;
retrieving substantially all of the predetermined amount of solvent from the void of the test chamber; and
measuring properties of the solvent to derive a level of contamination of the surface.

10. The method of claim 9, wherein the surface being tested for contaminants is a curved surface.

11. A system for testing a surface for contaminants, the system comprising:
the apparatus according to claim 1;
a dispensing tube for injecting and retrieving solvent to and from the apparatus of claim 1; and
a testing device configured to determine contaminant levels of a solvent.

12. An apparatus for facilitating testing a surface for contaminants, the apparatus comprising:
a test chamber; and
an overlay configured to be secured to a complementary surface of the test chamber;
the overlay including means for applying sufficient pressure onto the surface to be tested to form a water tight seal between the test chamber and the surface to be tested;
wherein the test chamber further comprises an internal circumferential wall and a dome-like roof, the internal circumferential wall and the dome-like roof of the test chamber cooperating with the surface to define a void, the test chamber further including a path extending through the internal circumferential wall of the test chamber from inside the void to outside the apparatus.

13. The apparatus of claim 12, wherein the overlay and the test chamber are integrally formed.

14. The apparatus of claim 12, wherein the dome-like roof of the test chamber is configured to be flexible and accommodate overfilling of the void with solvent.

15. A method of testing a surface for contaminants, the method comprising:
securing the apparatus described in claim 12 to the surface;
inserting a dispensing tube along the path from the void defined by an overlay orifice of the overlay and a test chamber orifice of the test chamber, the path extending from an external circumferential wall of the overlay to the internal circumferential wall of the test chamber;
depositing a predetermined amount of solvent into the void of the test chamber;
agitating the predetermined amount of solvent in the void of the test chamber;
retrieving substantially all of the predetermined amount of solvent from the void of the test chamber; and
measuring properties of the solvent to derive a level of contamination of the surface.

16. A system for testing a surface for contaminants, the system comprising:
the apparatus of claim 12;
a dispensing tube for injecting and retrieving solvent to and from the apparatus of claim 12; and
a testing device configured to determine contaminant levels of a solvent.

17. The apparatus of claim 12, wherein the pressure applying means includes at least one magnet on the overlay.

18. The apparatus of claim 12, wherein the pressure applying means includes an adhesive.

19. An apparatus for facilitating testing a surface for contaminants, the apparatus comprising:
a test chamber; and
an overlay configured to apply pressure onto a complementary surface of the test chamber;
wherein the test chamber further comprises an internal circumferential wall and a dome-like roof, the internal circumferential wall and the dome-like roof of the test chamber cooperating with the surface to define a void, the internal circumferential wall of the test chamber being an endpoint of a path extending from the void;
the test chamber further comprising an air-permeable water-resistant membrane.

* * * * *